United States Patent [19]

Whitesides et al.

[11] Patent Number: 4,814,469

[45] Date of Patent: Mar. 21, 1989

[54] NOVEL HYDROPEROXIDE AND USE OF SAME AS INTERMEDIATE FOR THE PREPARATION OF 3A,6,69A-TETRAMETHYLPERHYDRONAPHTHO[2,1-B]FURAN

[75] Inventors: George M. Whitesides, Newton, Mass.; René Decorzant, Onex; Ferdinand Naef, Carouge, both of Switzerland

[73] Assignee: Firmenich, SA, Geneva, Switzerland

[21] Appl. No.: 116,082

[22] Filed: Nov. 3, 1987

Related U.S. Application Data

[62] Division of Ser. No. 843,529, Mar. 25, 1986, Pat. No. 4,734,530.

[30] Foreign Application Priority Data

Mar. 26, 1985 [CH] Switzerland ............... 1313/85

[51] Int. Cl.$^4$ ............................................. C07D 307/77
[52] U.S. Cl. ..................................... 549/458; 568/567
[58] Field of Search ..................... 549/458; 568/567

[56] References Cited

U.S. PATENT DOCUMENTS 4,613,710  9/1986  Büchi et al. ..................... 549/458

Primary Examiner—Jane T. Fan
Attorney, Agent, or Firm—Pennie & Edmonds

[57] ABSTRACT

Novel hydroperoxide of formula

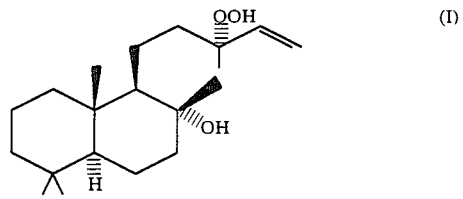

and use of same as intermediate for the preparation of 3a,6,6,9a-tetramethylperhydronaphtho[2,1-b]furan, also known as AMBROX (registered tradename of FIRMENICH SA, Geneva/Switzerland).

Process for its preparation via an oxidation of sclareol by means of hydrogen peroxide in the presence of an acidic agent.

12 Claims, No Drawings

NOVEL HYDROPEROXIDE AND USE OF SAME AS INTERMEDIATE FOR THE PREPARATION OF 3A,6,69A-TETRAMETHYLPERHYDRONAPHTHO[2,1-B]FURAN

This is a division of application Ser. No. 843,529, filed Mar. 25, 1986 now U.S. Pat. No. 4,734,530, issued Mar. 29, 1988.

BRIEF SUMMARY OF THE INVENTION

Novel hydroperoxide of formula

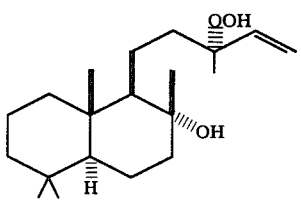
(I)

under the form of an epimeric mixture or as pure isomers of formula (Ia)+(Ib)

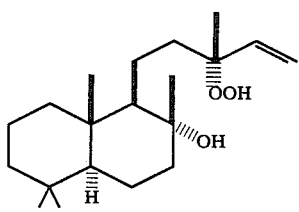
(Ia)

and

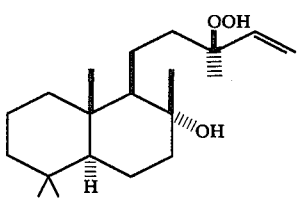
(Ib)

Said hydroperoxide is useful as an intermediate for the preparation of 3a,6,6,9a-tetramethylperhydronaphtho[2,1-b]furan (known under its registered tradename AMBROX, origin FIRMENICH SA, Geneva/Switzerland); this preparation occurs via a treatment of hydroperoxide (I) with a redox reagent consisting of the couple $Fe^{II}/Cu^{II}$.

The preparation of novel hydroperoxide (I) occurs by oxidation of sclareol by means of hydrogen peroxide.

BACKGROUND OF THE INVENTION

The present invention relates to the field of perfumery. It provides in particular a new process for the preparation of 3a,6,6,9a-tetramethylperhydronaphtho[2,1-b]furan, a compound of formula

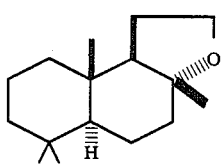

known in the art under the name of AMBROX. Owing to its olfactive characters of ambergris type and its power of diffusiveness, AMBROX has become over the years an essential ingredient in numerous perfume compositions of various nature.

Since its discovery [see Helv. Chim. Acta 33, 1251 (1950)], several syntheses have been proposed by different research groups. These are generally based on an oxidative degradation reaction of diterpene compounds such as (−)-sclareol or (+)-manool, or they use ambreine as starting material [G. Ohloff in fragrance Chemistry, Ed. Ernst T. Theimer, p. 545, Academic Press (1982)]. This synthetic approach can be illustrated by means of the following reaction scheme:

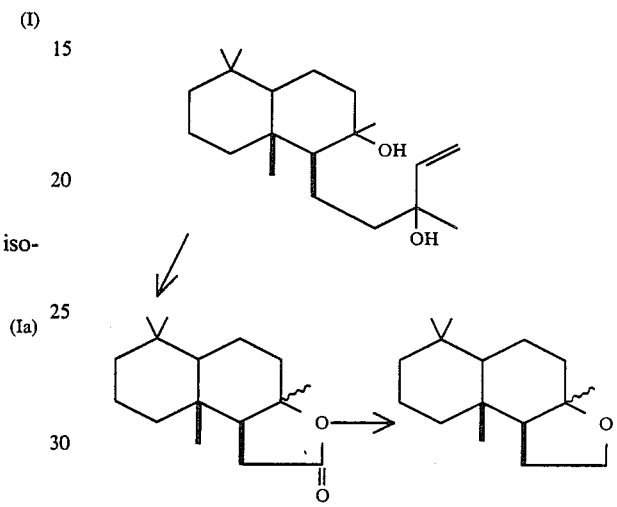

Due to the fact that the above cited starting materials are of natural origin and that the yields for their extraction from the natural sources are small, it is necessary, in order to reduce the price, to dispose of an industrial manufacturing process which can offer improved yields.

The present invention provides a novel and original solution to the problem of preparing AMBROX.

THE INVENTION

The present invention provides an intermediate for the preparation of AMBROX which compound is defined by formula

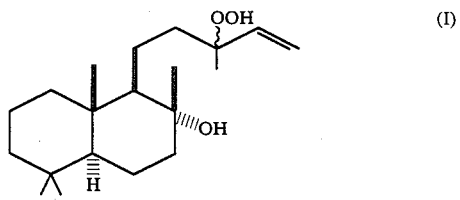
(I)

Said formula is deemed to define indifferently one or the other of the epimeric compounds of formula (Ia) and (Ib), respectively

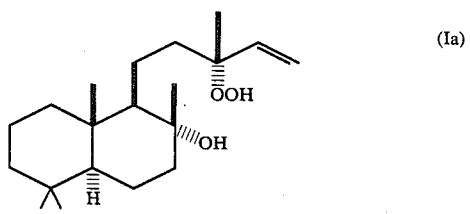
(Ia)

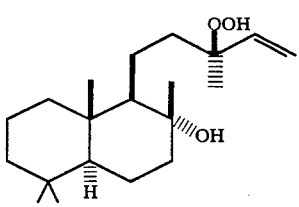

or any mixture thereof.

According to the invention, hydroperoxides of formula (I) are prepared by a process which comprises the oxidation of sclareol by means of hydrogen peroxide in the presence of an acidic agent followed by the separation of the desired products from the reaction mixture by means of column chromatography. Thus, by said oxidation, the desired compound is directly obtained under the form of an epimeric mixture which can then be subjected to crystallization in hexane to give pure epimers (Ia) and (Ib).

Suitable acidic agents include an organic protonic acid such as p-toluenesulfonic acid.

Hydroperoxide of formula (I), either as a mixture or in the form of each isolated pure epimer, can be used as a starting material for the preparation of AMBROX.

The present invention provides a process according to which this latter compound is obtained by treating hydroperoxide (I) with a redox reagent consisting of a couple $Fe^{II}/Cu^{II}$.

The overall process is illustrated by the following reaction pathway:

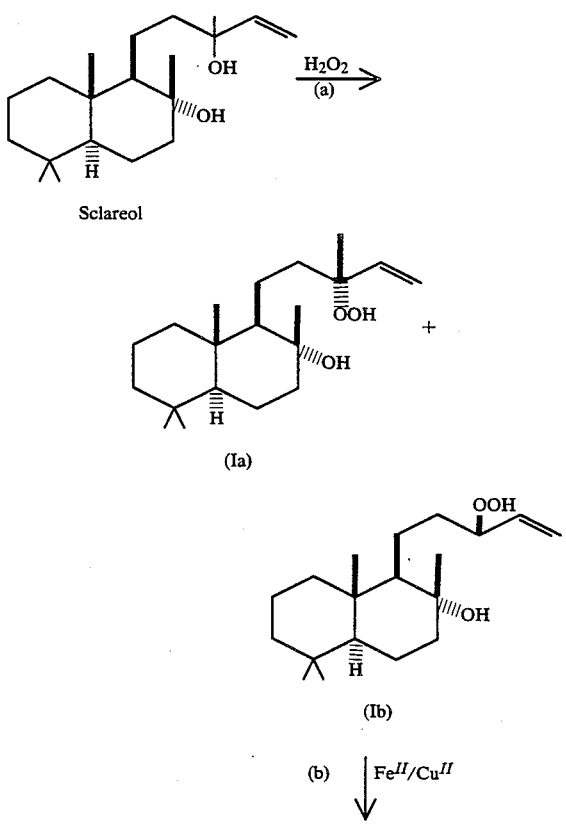

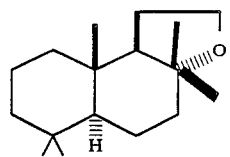

AMBROX

The reaction defined in step (a) of the above process can be carried out either in the presence of an inert solvent, or in the absence of it. Preferred inert solvents include halogenated hydrocarbons such as e.g. methylene chloride. The oxidation is effected, as indicated above, by means of aqueous solutions of hydrogen peroxide at various concentration. Concentrations of the order of 50% (v/v) or more are perfectly adapted for such an operation.

Concerning the redox couple $Fe^{II}/Cu^{II}$, it is possible to use conventional organic or inorganic salts of copper and iron, e.g. copper(II) acetate and iron(II) sulphate. The reaction is carried out in an alcoholic medium and to this end, an aliphatic alcohol, e.g. methanol, is used.

The invention is better illustrated by, but not limited to the following examples wherein the temperatures are indicated in degrees centigrade and the abbreviations have the meaning common in the art.

EXAMPLE 1

Preparation of the hydroperoxide of formula (I)

A mixture consisting of 30.8 g (0.1M) of sclareol, 200 ml of methylene chloride, 100 ml of 70% hydrogen peroxide in water and 0.2 g of p-toluenesulphonic acid was kept under stirring at room temperature for 7 days. The organic layer, once separated, was washed with water, dried over MgSO4 and concentrated in a rotary evaporator under vacuum by taking care that the temperature of the mixture does not raise beyond 25°. 35 G of a raw material was thus obtained. By purification on a column chromatography over silicagel (Merck 0.2–0.063; 350 g; eluant: cyclohexane/ether at 7:3 to 0:1), a fraction consisting of 19.7 g was obtained. This consisted of a mixture of the desired hydroperoxides (Ia) and (Ib) together with a compound of formula

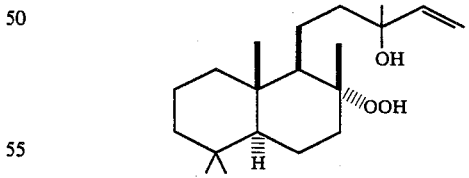

accompanied by some impurities of undefined nature.

1 G of the obtained fraction was chromatographed on two Merck type columns assembled in series (LOBAR, registered tradename, dimension B, 310–23 mm) and filled with LiChropen (registered tradename), Si 60, 40–63 mm, art. 10401. The elution is carried out with a mixture of cyclohexane/ethyl acetate (7:3) at a pressure of about 20 psi. There were thus obtained 629 mg of an epimeric mixture (Ia)/(Ib) which, upon crystallization in hexane at a temperature of between about +25° and −20°, gave epimer (Ia) having m.p. 113°–4°.

The analytical characters of the obtained compounds were the following:

(Ia): NMR (360 MHz; CDCl$_3$): 0.80; 0.81; 0.87 (3s, 3x3H); 1.19 (1s, 3H); 1.22 (1s, 3H); 5.13 (dxd; J$_1$=2, 1H); 5.19 (dxd, J$_1$=18, J$_2$=2, 1H), 6.04 (dxd, J$_1$=11, J$_2$=18, 1H) δppm;

(Ib): NMR (360 MHz; CDCl$_3$): 0.80; 0.81; 0.87 (3s,3x3H); 1.20 (s, 3H); 1.34 (s, 3H); 5.14 (dxd, J$_1$=2, 1H); 5.19 (dxd, J$_1$=18, J$_2$=2, 1H); 5.81 (dxd, J$_1$=11, J$_2$=18, 1H) δppm.

EXAMPLE 2

Preparation of AMBROX 0.47 G (1.45 mM) of the mixture of hydroperoxide (Ia)/(Ib) obtained according to Example 1, were dissolvedin methanol and treated with 0.435 g (2 mM) of Cu(OAc)$_2$.2H$_2$O (Ac=CH$_3$CO) and 0.417 g (1.5 mM) of FeSO$_4$.7H$_2$O. The resulting suspension was kept under stirring at 50° for 2 hours whereupon the reaction mixture was concentrated under reduced pressure by taking care that its temperature does not raise above 25°. The residue was diluted with water and extracted with ether, then the combined ethereal extracts were washed with water, dried over MgSO$_4$ and concentrated. They were then filtered through 1 g of silicagel(-solvent: ether). The evaporation of the solvent gave 0.355 g of a product containing 60% of AMBROX.

The raw material was then chromatographed on silicagel (20 g; eluant: cyclohexane/ether, 9:1) to yield 87 mg (yield 30%) of pure crystalline AMBROX. The table hereinbelow summarizes the obtained results together with the reaction conditions applied in the course of several asseys for the preparation according to the above indicated procedure.

TABLE

| Mixture (Ia)/(Ib) [mM] | Cu$^{II}$ salt [mM] | Fe$^{II}$ salt [mM] | solvent [ml] | temp. [°C.] | reaction time [h] | yield Ambrox [%] |
| --- | --- | --- | --- | --- | --- | --- |
| 6.2 | 2 | 15 | 20 | 50 | 3 | 32 |
| 6.2 | 2 | 15 | 20 | 65 | 3 | 31 |
| 6.2 | 2 | 2 | 20 | 50 | 3 | 25 |
| 6.2 | 2 | 1 | 20 | 50 | 3 | 25 |
| 6.2 | 10 | 7 | 20 | 50 | 3 | 33 |
| 6.2 | 10 | 7 | 200 | 50 | 3 | 32 |

What we claim is:

1. A process for the preparation of 3a,6,6,9a-tetramethylperhydronaphtho[2,1b]furan, which comprises treating an epimeric mixture of hydroperoxides of the formula:

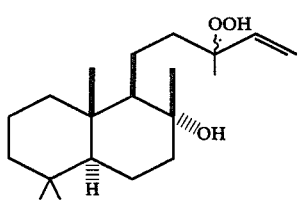

with a redox reagent consisting of the couple Fe$^{II}$/Cu$^{II}$ to form

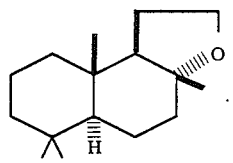

2. The process according to claim 1, wherein the couple Fe$^{II}$/Cu$^{II}$ is Fe(II) sulphate and Cu(II) acetate.

3. The process according to claim 1, wherein the reaction is effected in an alcoholic medium.

4. The process of claim 1 wherein the epimeric mixture of hydroperoxides is prepared by oxidizing sclareol with hydrogen peroxide in the presence of an acidic agent and separating thereafter the desired epimeric mixture from the reaction mixture.

5. The process according to claim 4, wherein the acidic agent is p-toluene-sulfonic acid.

6. The process according to claim 4, wherein hydrogen peroxide is used at a concentration higher than 50% (v/v) in water.

7. A process for the preparation of 3,a,6,6,9a-tetramethylperhydronaphtho[2,1-b]furan, which comprises treating an epimeric mixture of the formula:

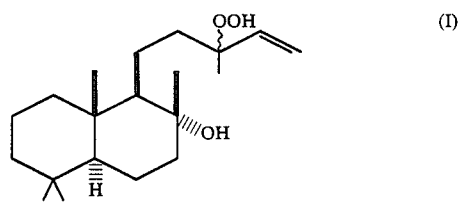

with a redox reagent of the couple Fe(II) sulphate/-Cu(II) acetate in an alcoholic medium to form

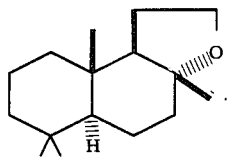

8. The process of claim 7 wherein the epimeric mixture is prepared by oxidizing sclareol with hydrogen peroxide in the presence of an acidic agent and separating thereafter the desired epimeric mixture from the reaction mixture via column chromatography.

9. The process according to claim 8, wherein the acidic agent is p-toluene-sulfonic acid.

10. The process according to claim 8, wherein hydrogen peroxide is used at a concentration higher than 50% (v/v) in water.

11. A process for the preparation of 3a,6,6,9a-tetramethylperhydronaphtho(2,1-b)furan, which comprises:
   oxidizing sclareol with hydrogen peroxide having a concentration of greater than 50% (v/v) in water in the presence of an acidic agent of p-toluene-sulfonic acid to form an epimeric mixture of hydroperoxides of the formula:

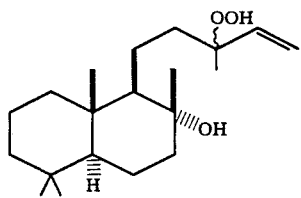 (I)
separating the epimeric mixture of hydroperoxides from the reaction mixture by column chromatography; and
treating the epimeric mixture of hydroperoxides with a refox reagent consisting of the couple $Fe^{II}/Cu^{II}$ in an alcoholic medium to form
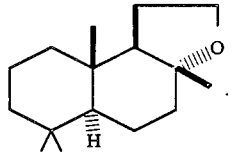
12. The process according to claim 11, wherein the couple $Fe^{II}/Cu^{II}$ is Fe(II) sulphate and Cu(II) acetate.
* * * * *